United States Patent

Bonini et al.

[11] Patent Number: 6,066,764
[45] Date of Patent: May 23, 2000

[54] PRODUCTION OF 3-CHLORO-4-FLUORO-BENZOYL CHLORIDE BY LEWIS-ACID CATALYZED CHLORINATION OF THE AROMATIC RING

[75] Inventors: Dino Bonini; Damiano Torrente; Filippo Maria Carlini, all of Trissino Vi, Italy

[73] Assignee: Miteni S.p.A., Trissino, Italy

[21] Appl. No.: 09/151,645

[22] Filed: Sep. 10, 1998

[30] Foreign Application Priority Data

Sep. 23, 1997 [IT] Italy .................... MI97A2146

[51] Int. Cl.[7] ............................ C07C 51/58; C07C 51/64
[52] U.S. Cl. ............................ 562/866; 562/864
[58] Field of Search ................... 562/864, 866

[56] References Cited

U.S. PATENT DOCUMENTS 4,315,766  2/1982  Hamprecht et al. .

OTHER PUBLICATIONS

Kirk–Othmer Encyclopedia of Chemical Technology; Wiley–Interscience; vol. 6, pp. 90–92, 1993.
Adams et al. J. Am Chem Soc.; vol. 72; p. 2454, 1950.
Carey, Organic Chemistry; McGraw–Hill; New York; Table 13.1 p 452, 1987.
Weissberger, A.; Ed.; Techniques of Organic Chemistry, vol IV: Distillation; Interscience, New York; table of contents, 1951.

Primary Examiner—Gary Geist
Assistant Examiner—Robert W. Deemie
Attorney, Agent, or Firm—Collard & Roe, P.C.

[57] ABSTRACT

The present invention relates to halogenated aromatic derivatives, in particular 3-chloro-4-fluoro-benzoyl chloride having the following formula:

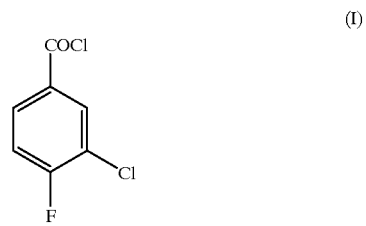

The aforesaid derivative is advantageously used as base product for the preparation of fluorinated compounds employed in their turn as active principles in the pharmaceutical and agricultural fields as well as in dye industry.

The present invention also relates to a process for the preparation of 3-chloro-4-fluoro-benzoyl chloride that allows to obtain the end compound with high selectivity, high yields and one only step starting from a known and commercially available product

8 Claims, No Drawings

PRODUCTION OF 3-CHLORO-4-FLUORO-BENZOYL CHLORIDE BY LEWIS-ACID CATALYZED CHLORINATION OF THE AROMATIC RING

DESCRIPTION

OBJECT OF THE INVENTION

The present invention relates to halogenated aromatic derivatives, in particular fluorinated aromatic derivatives, and their use as base products for the preparation of fluorinated compounds employed as active principles in the pharmaceutical and agricultural fields as well as in dye industry.

The present invention further relates to a process for the preparation of said halogenated aromatic derivatives.

DESCRIPTION OF THE INVENTION

As is known, aromatic base fluorinated compounds are of great importance in several fields of chemistry and have been studied for a long time because of their particular properties. Such compounds are mainly applied in the pharmaceutical and agricultural fields as well as in dye industry.

For instance, in the pharmaceutical field, many compounds are known that are employed as active principles and that comprise in their chemical structure an aromatic ring variously substituted with halogens, in particular with one or more fluorine atoms; the presence of such fluorinated aromatic ring imparts generally the compound a great part of its activity and is therefore indispensable within its structure.

In the same way, also in the agricultural field, many compounds are known that are employed as active principles and whose structure is based on the presence of at least a fluorinated aromatic ring, which imparts the compound its activity and is therefore determinant for its use as an active principle in a specific field. Generally, the aforesaid active principles are stable and effective also thanks to the inherent characteristics of the carbon-fluorine bond which is present in the structure; such bond in fact is more stable and iso-geometrical compared with the corresponding carbon-hydrogen bond.

Therefore, the importance is obvious of providing halogenated aromatic derivatives, in particular fluorinated ones utilisable as base products for the preparation of fluorinated compounds to be employed in their turn as active principles in several fields, for instance in the pharmaceutical and agricultural fields as well as in dye industry.

The necessity is as much obvious of the availability of said halogenated aromatic derivatives having a high degree of purity, in particular as concerns the presence of possible isomers of the same derivative, as their use as base products for the preparation of fluorinated compounds, employed in their turn as active principles in the above indicated sectors, requires a high degree of purity, in order to ensure the activity of the active principle.

Object of the present invention is therefore to provide an halogenated aromatic derivative, in particular a fluorinated one, constituting the base product of fluorinated compounds employed as active principles in the pharmaceutical and agricultural fields as well as in dye industry.

A further object of the present invention is to provide a process for the preparation of an halogenated aromatic derivative, in particular a fluorinated one, such as to allow to obtain said derivative with a high degree of purity compared to possible by-products constituted, for instance, by isomers of said derivative.

Still a further object of the present invention is to provide a process for the preparation of an halogenated aromatic derivative, in particular a fluorinated one, advantageous from the economic point of view, such as not to require many steps and as to be applicable on an industrial scale.

These and still other objects, which will be stressed by the following description, are achieved by an halogenated aromatic derivative having the following formula:

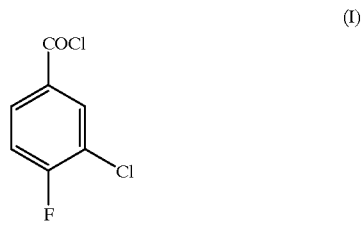

(I)

Said derivative (I), 3-chloro-4-fluoro-benzoyl chloride, is advantageously used as base product for the preparation of fluorinated compounds employed in their turn as active principles in the pharmaceutical and agricultural fields as well as in dye industry.

According to the present invention, a process for the preparation of said derivative (I) has the synthesis scheme shown hereunder:

SCHEME 1

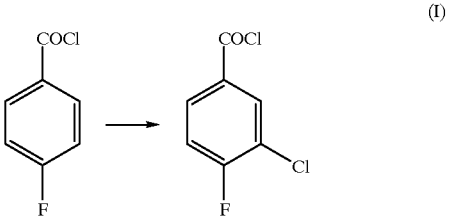

(I)

4-fluoro-benzoyl chloride, a commercially available substance, having been submitted, if necessary, to purification, for instance by distillation, is subjected to a chlorination reaction, in the presence of Lewis acids, at temperatures of from 60 to 130° C., and in the presence of gaseous chlorine, preferably in excess. The conversion is carried out up to 40–90%, preferably 60–90%, in a period of time of from 8 to 16 hours, in order to reduce the polychlorinated products. Said reaction is preferably carried out at temperatures of from 80 to 110° C., and said Lewis acid is selected from among $AlCl_3$, $ZnCl_2$, and preferably $FeCl_3$.

The end product, 3-chloro-4-fluoro-benzoyl chloride (I), is separated from excess reactant, for instance by fractional distillation. The so separated reactant may be directly recycled to chlorination in a further reaction cycle.

In particular, the process according to the invention allows to obtain 3-chloro-4-fluoro-benzoyl chloride (I) with a low content (generally lower than 0.5%) of 2-chloro-4-fluoro-benzoyl chloride isomer, which is of major importance as the two isomers have boiling points that are very close to each other (about 0.5° C. of difference), and their separation with conventional techniques would be therefore difficult. To this aim, the chlorination reaction carried out on 4-fluoro-benzoyl chloride according to the present invention allows to obtain the end product with the required characteristics.

It is therefore obvious that the above process allows to selectively obtain 3-chloro-4-fluoro-benzoyl chloride (I), does not require further purifications of the end product and is advantageous from the economic point of view. This is of great importance from the industrial point of view, as by selectively obtaining the desired product the necessity is eliminated of carrying out further purification steps, often expensive, which involve a drastic drop in yields, with an ensuing cost increase.

With reference to the process of Scheme 1, there are reported hereunder some examples of actual implementation, solely given by way of non limiting examples of the present invention.

EXAMPLE 1

100 g of 4-fluoro-benzoyl chloride and 0.5 g of $FeCl_3$ are charged in a 250 ml flask. The mass is heated to a temperature of 80° C. and chlorine is fluxed at a rate of about 1 Nl/h.

After 16 hours of reaction, the raw product is cooled, degassed with nitrogen and discharged.

The product is vacuum distilled (15 mmHg) to separate the non converted reactant. 35 g of 4-fluoro-benzoyl chloride, 66 g of 3-chloro-4-fluoro-benzoyl chloride (I) and 10 g of impurities are obtained. Yield: 83.4%.

EXAMPLE 2

100 g of 4-fluoro-benzoyl chloride and 0.3 g of $FeCl_3$ are charged in a 250 ml flask. The mass is heated to a temperature of 110° C. and chlorine is fluxed at a rate of about 1 Nl/h.

After 16 hours of reaction, the raw product is cooled, degassed with nitrogen and discharged.

The product is vacuum distilled (15 mmHg) to separate the non converted reactant. 28 g of 4-fluoro-benzoyl chloride, 72 g of 3-chloro-4-fluoro-benzoyl chloride and 18 g of impurities are obtained. Yield: 821%.

What is claimed is:

1. A process for the preparation of 3-chloro-4-fluoro-benzoyl chloride (I) according to the following scheme:

SCHEME 1

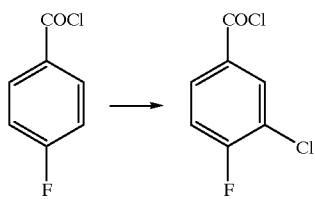

comprising, starting from 4-fluoro-benzoyl chloride the following steps:
  possible purification of said 4-fluoro-benzoyl chloride;
  chlorination reaction of said 4-fluoro-benzoyl chloride, obtaining 3-chloro-4-fluoro-benzoyl chloride (I);
  possible separation of 3-chloro-4-fluoro-benzoyl chloride (I) from excess reactant.

2. The process according to claim 1, characterised in that said purification step of said 4-fluoro-benzoyl chloride is a distillation step.

3. The process according to claim 1, characterised in that said chlorination reaction of said 4-fluoro-benzoyl chloride is mass-conducted and carried out in the presence of at least a Lewis acid, at temperatures of from 60 to 130° C., and in the presence of gaseous chlorine.

4. The process according to claim 3, characterised in that said Lewis acid is $FeCl_3$.

5. The process according to claim 1, characterised in that said possible separation of 3-chloro-4-fluoro-benzoyl chloride (I) from excess reactant is carried out by fractional distillation.

6. The process according to claim 3, characterised in that said temperature is of from 80 to 110° C.

7. The process according to claim 1, characterised in that the conversion of the reactant is carried out up to between 40 and 90%.

8. The process according to claim 7, characterised in that the conversion is carried out up to between 60 and 90%.

* * * * *